United States Patent [19]

Namekawa et al.

[11] Patent Number: 4,573,477

[45] Date of Patent: Mar. 4, 1986

[54] ULTRASONIC DIAGNOSTIC APPARATUS

[75] Inventors: Koroku Namekawa; Akira Koyano; Chihiro Kasai, all of Tokyo, Japan

[73] Assignee: Aloka Co., Ltd., Tokyo, Japan

[21] Appl. No.: 487,147

[22] Filed: Apr. 21, 1983

[30] Foreign Application Priority Data

Apr. 28, 1982 [JP] Japan .................................. 57-70479

[51] Int. Cl.[4] .............................................. A61B 10/00
[52] U.S. Cl. .................................. 128/663; 73/861.25
[58] Field of Search ............................... 128/660, 663; 73/861.25, 861.06

[56] References Cited

U.S. PATENT DOCUMENTS

| 3,844,170 | 10/1974 | Critten | 73/861.06 |
| 4,201,083 | 5/1980 | Kurita et al. | 73/861.06 |
| 4,324,258 | 4/1982 | Huebscher et al. | 128/663 |
| 4,334,543 | 6/1982 | Fehr | 128/663 |

OTHER PUBLICATIONS

Nowicki et al., *An Infinite Gate Pulse Doppler*, Ultrasound in Med. & Biol., vol. 7/No. 1, pp. 41–50, Feb. 1981.
Brandestini, *Topoflow–A Digital Full Range Doppler Velocity Meter*, IEEE Transactions on Sonics and Ultrasonics, vol. SU–25, No. 5, Sep. 1978, pp. 287–293.
Brandestini et al., *Blood Flow Imaging Using a Discrete Time Frequency Meter*, IEEE Ultrasonics Symposium Proceedings, Cat. #78, Ch. 1344-ISU, Sep. 1978, pp. 348–352.

*Primary Examiner*—William E. Kamm
*Assistant Examiner*—Ruth S. Smith
*Attorney, Agent, or Firm*—Koda and Androlia

[57] ABSTRACT

An ultrasonic diagnostic apparatus for accurately displaying the velocity distribution of moving members within a living organism. The apparatus constitutes an improvement on the ultrasonic diagnostic apparatus of the type wherein an ultrasonic pulse beam is repeatedly transmitted into the living organism at a fixed pulse rate and the reflected echoes are picked up, amplified and displayed, wherein the improvement comprises a complex signal converter for converting a received high frequency signal into complex signals by mixing the received high frequency signal with a pair of complex reference signals which have frequencies that are integer multiples of the pulse rate and which are complexly related to one another, an autocorrelator for determining the autocorrelation of the complex signals, the autocorrelator having a delay time equal to an integer multiple of the pulse period, and a velocity determination circuit for determining the velocity through said autocorrelation. The apparatus is capable of measuring the velocity distribution of moving members within the organism and of rapidly displaying the measured results in real time.

2 Claims, 1 Drawing Figure

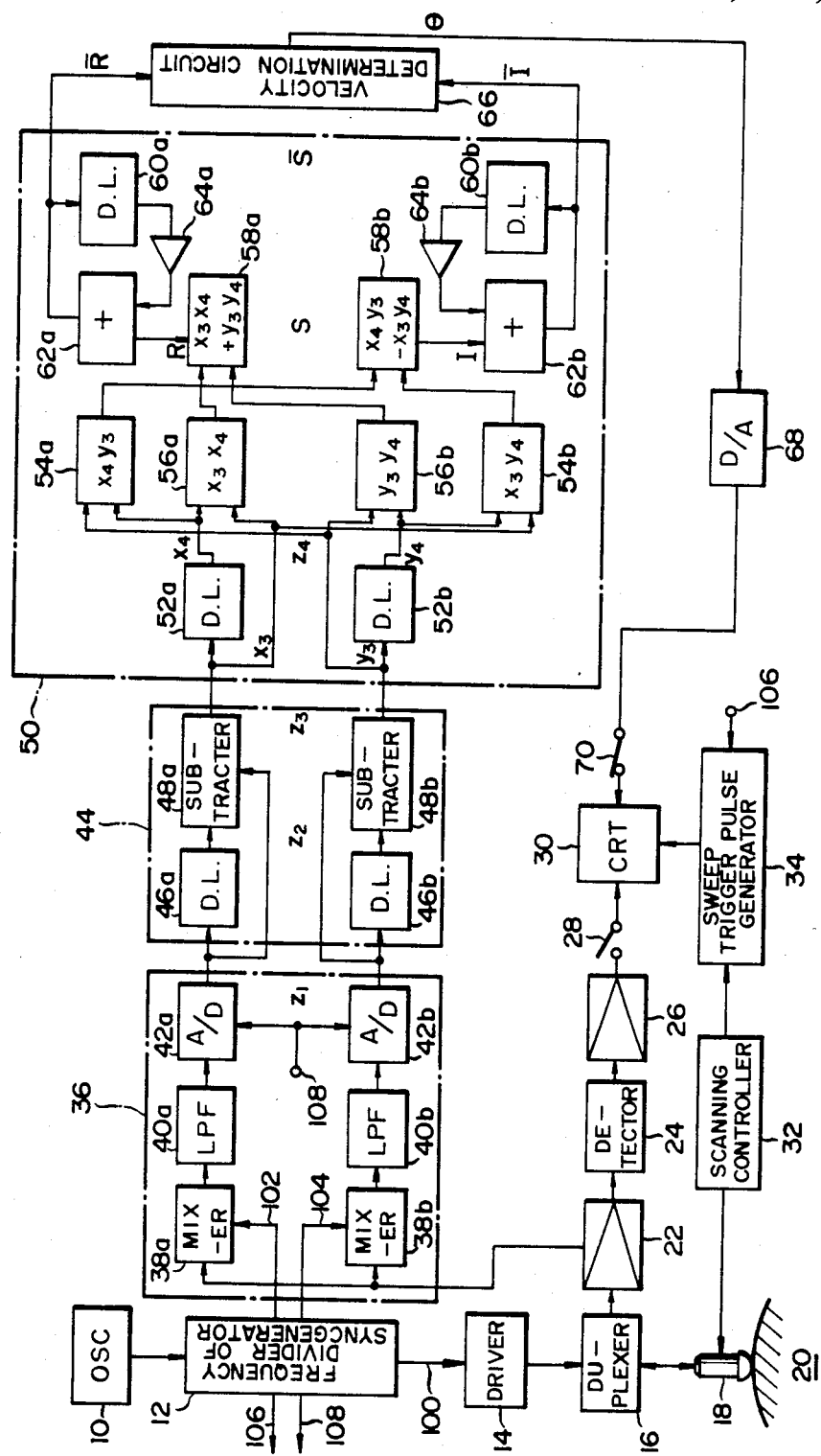

4,573,477

ULTRASONIC DIAGNOSTIC APPARATUS

BACKGROUND OF THE INVENTION

1. Field of the Invention

This invention relates to an ultrasonic diagnostic apparatus, more particularly to an improved ultrasonic diagnostic apparatus which is capable of accurately displaying the velocity distribution of movement of moving members within a living organism.

2. Description of the Prior Art

The ultrasonic pulse-Doppler method has been practically applied to the measurement of the velocity of movement of a body organ such as the heart, of blood flowing in the blood vessels or of other body fluids. The conventional apparatus for applying this method electrically detects the velocity of movement from the frequency shift of an echo reflected from the moving members within the living body but is capable of detecting the velocity of movement only at a specific point at a prescribed depth within the organism. Therefore, in order to obtain the velocity distribution of, for example, flowing blood over a wide target region, it is necessary to repeat the process of sending and receiving ultrasonic pulses many times for many different target points and then to obtain the distribution by synthesizing the results obtained. The process is thus very time consuming. As a consequence, the measurement of the velocity distribution by this method cannot closely follow the changes in the moving members of the organism and, in particular, it is impossible to realize real-time observation of the changes in the blood flow condition caused by pulsation.

As an improved ultrasonic pulse-Doppler apparatus there has been proposed one provided with a plurality of channels so as to make it possible to obtain information on the velocity distribution of flowing blood over a desired region in a single measurement. However, since this improved apparatus, like conventional Doppler apparatuses, has only a narrow band width (usually of only several kHz), it is not capable of collecting Doppler information rapidly, making it difficult to observe the changes in the blood flow condition in B-mode scanning. Also, as it must be provided with many channels, it has the drawbacks of being bulky and costly.

SUMMARY OF THE INVENTION

In view of the above-mentioned disadvantages inherent in conventional apparatuses, it is the object of the present invention to provide an improved ultrasonic diagnostic apparatus which, through improvement of the ultrasonic pulse-Doppler method, is capable, without need to resort to the conventional multichannel system, of determining in a single measurement the velocity distribution of movement along the scanning line of a sent and received ultrasonic pulse beam and of representing the measured velocity distribution at high speed in real time.

In order to attain this object, the present invention provides an improved ultrasonic diagnostic apparatus of the type wherein an ultrasonic pulse beam is repeatedly transmitted into a living organism at a fixed pulse rate and the reflected echoes are picked up, amplified and displayed as the velocity of movement within the organism, the improvement comprising a complex signal converter for converting a received high frequency signal into complex signals by mixing the received high frequency signal with a pair of complex reference signals which have frequencies that are integer multiples of the pulse rate and which are complexly related to one another, an autocorrelator for determining the autocorrelation of said complex signals, and a velocity determination circuit for determining the velocity through said autocorrelation, whereby the velocity distribution of the moving members in the living organism is measured and displayed.

BRIEF DESCRIPTION OF THE DRAWING

The single FIGURE is a block circuit diagram of an embodiment of the ultrasonic diagnostic apparatus according to the present invention.

DESCRIPTION OF THE PREFERRED EMBODIMENT

A crystal oscillator 10 produces a stable high frequency signal which is forwarded to a frequency divider and sync generator 12 for producing a number of output signals of desired frequencies. These output signals include a pulse rate signal 100 used for transmission of an ultrasonic pulse beam, complex reference signals 102, 104 for complex conversion, a sweep synchronizing signal 106 for use in displaying the results of the ultrasonic diagnosis, and a clock signal 108 for synchronizing the various sections of the apparatus. In this invention, the complex reference signals 102, 104 are of frequencies which are integer multiples of the pulse rate signal 100 and are phase-shifted from one another, by 90° in this embodiment, so as to be in a complex relationship.

The transmission signal 100 is supplied to a probe 18 through a driver 14 and a duplexer 16 and upon being excited by this signal, the probe 18 transmits an ultrasonic pulse beam into a specimen 20.

The echo reflected by the specimen 20 is converted into an electrical signal by the probe 18 and is forwarded through the duplexer 16 to a high frequency amplifier 22 by which it is amplified to a prescribed degree and output in two separate directions: to a display section as an ordinary B-mode or M-mode display signal and to an arithmetic processing section provided in accordance with this invention for determining the velocity of movement.

The signal output from the high frequency amplifier 22 for carrying out ordinary B-mode or M-mode display is supplied to a cathode ray tube (CRT) display 30 via a detector 24, a video amplifier 26 and a switch 28.

A scanning controller 32 is provided for angularly deflecting the ultrasonic pulse beam from the probe 18, either mechanically or electrically, so as to periodically scan the specimen 20, or for halting the scanning operation at a desired deflection angle. This scanning position signal from the scanning controller 32 and the sweep synchronizing signal 106 from the frequency divider and sync generator 12 are supplied to a sweep trigger pulse generator 34 to sweep-control the CRT display 30.

The other output from the high frequency amplifier 22 is subjected to complex processing in accordance with this invention in order to obtain information on the velocity of movement. For this purpose, the received high frequency signal from the high frequency amplifier 22 is forwarded to a complex signal converter 36 for conversion into a complex signal.

More specifically, in this embodiment, the complex signal converter 36 comprises a pair of mixers 38a, 38b, each of which includes a phase detector. The above received high frequency signal is processed with the complex reference signals 102, 104 in the respective mixers 38 and since the complex reference signals 102, 104 are in a complex relationship, namely since they are 90° out of phase, it is possible to obtain from the mixers 38 complex signal outputs corresponding to the received high frequency signal. More precisely, by means of mixing and detection, each of the mixers 38 outputs two signals, one with a frequency equal to the sum of and the other with a frequency equal to the difference between the frequencies of the received high frequency signal and the complex reference signal. The outputs of the mixers are then forwarded to the low pass filters 40a, 40b which pass only the difference frequency component of each.

Thus, as a result of the mixing and detection operation carried out by the aforesaid mixers 38, the complex reference signals 102, 104 are single-frequency continuous waves, whereas the input signal, namely the received high frequency signal, is a pulse wave including Doppler information. As a result, the outputs from the low pass filters 40 include a large number of spectral components. This complex conversion will now be explained through the use of conversion formulas.

The complex reference signal 102 has a frequency $f_o$ which is an integer multiple of the frequency $f_r$ of the pulse rate signal 100 for the high frequency transmission signal and if the amplitude of this complex reference signal 102 is taken as 1, then it can be represented as the following sine wave voltage signal:

$$\sin 2\pi f_o t \qquad (1)$$

On the other hand, if the transmission frequency is taken as $f_o$, then the high frequency signal received by the probe 18 can be expressed as $$\sin (2\pi f_o t + 2\pi f_d t) \qquad (2),$$

wherein $f_d$ is the Doppler shift frequency.

Although, in general terms, this received signal includes the spectrum $$\sin\left\{ 2\pi(f_o \pm nf_r)t + 2\pi f_d\left(1 \pm n\frac{f_r}{f_o}\right) t \right\}$$

(wherein $f_r$ is the frequency of the pulse rate signal and n is a natural number such as 0, 1, 2 . . . ), in order to simplify the explanation, only the spectrum in the case where n=0 in formula (2) will be considered in the following.

As the product of the complex reference signal 102 and the received high frequency signal is obtained in the mixer 38a, it is possible to derive the output expressed as the following formula which is equal to twice the product of formulas (1) and (2)

$$\cos 2\pi f_d t - \cos (4\pi f_o t + 2\pi f_d t)$$

Then, since the frequency $2f_o$ is eliminated from this output by the low pass filter 40a, the output signal becomes $$\cos 2\pi f_d t \qquad (3)$$

On the other hand, since the complex reference signal 104 is out of phase by 90° with the signal 102, it can be expressed as the following cosine voltage signal $$\cos 2\pi f_o t \qquad (4),$$

and upon being mixed and detected in the mixer 38b and then passed through the filter 40b is converted to $$\sin 2\pi f_d t \qquad (5),$$

thus producing a complex signal having a real component as represented by formula (3) and an imaginary component as represented by formula (5). These signals can be expressed by the following complex formula $$z_1 = \cos 2\pi f_d t + i \sin 2\pi f_d t \qquad (6).$$

The signals $z_1$ thus obtained by complex conversion are then converted to digital signals by A/D converters 42a, 42b, whereafter they are forwarded to a complex delay-line canceller 44. The clock signal 108 is supplied to the A/D converters 42 where it is used to carry out sampling.

As the embodiment is provided with the complex delay-line canceller 44, it is possible to eliminate the portions of the signal received from the stationary or slow moving members within the living organism and to obtain velocity signals for only the moving portions, thus realizing a great improvement in the quality of the video signal. For example, consider the case of blood flow signals obtained from the living organism. Ordinarily, these signals are contaminated with what is known as clutter, namely echoes from such nearly stationary tissues of the living organisms as the walls of the blood vessels and the heart. As this clutter is ordinarily stronger than the blood flow signals, it constitutes a major hindrance to the measurement of the blood flow velocity. In this embodiment, however, since the signals from such low velocity members are eliminated by the complex delay-line canceller 44, it is possible to obtain the signals from the moving members of the living organism uncontaminated by other extraneous signals.

The delay-line canceller 44 has a pair of delay lines 46a, 46b each of which has a delay time equal to one period T of the pulse rate signal 100. These delay lines may, for example, be constituted of a number of memories or shift registers equal to the number of clock pulses per one period T. The delay lines 46a, 46b are connected with subtracters 48a, 48b which successively compare the inputs to the delay lines 46a, 46b (i.e. the signals during the current period T) with the outputs thereof (i.e. the signals during the preceding period T) at the same depth and calculate the difference between consecutive periods T. Therefore, since in the case of the echo signals from the stationary and slow moving parts of the living organism there is little or no difference between the current and preceding periods, the output of the subtracters 48a, 48b approaches zero, and, on the other hand, the signals for the high velocity portions, for example the blood flow signals, are obtained as large outputs. Thus, the aforesaid clutter can be suppressed to a very high degree.

The operation of the complex delay-line canceller 44 will now be explained with reference to the following formulas. Although in the FIGURE digital signals are input to the delay-line canceller 44, for simplicity of explanation, the following discussion will be based on the analog signals represented by formula (6). When the input signals $z_1$ applied to the delay lines 46 are as represented by formula (6), the output $z_2$ delayed by one period becomes $$z_2 = \cos 2\pi f_d(t-T) + i \sin 2\pi f_d(t-T) \qquad (7)$$

As a result, the difference outputs of the subtracters 48 become $$z_3 = z_1 - z_2 = -2 \sin 2\pi f_d \frac{T}{2} \sin 2\pi f_d \left(t + \frac{T}{2}\right) +$$

$$i\, 2 \sin 2\pi f_d \frac{T}{2} \cos 2\pi f_d \left(t + \frac{T}{2}\right)$$

and if the difference output $z_3$ is expressed as $$z_3 = x_3 + i y_3$$

then $x_3$, $y_3$ can be obtained as follows $$x_3 = -2 \sin 2\pi f_d T/2 \sin 2\pi f_d(t+T/2) \qquad (8)$$

$$y_3 = 2 \sin 2\pi f_d T/2 \cos 2\pi f_d(t+T/2) \qquad (9)$$

Therefore, in accordance with the above, the signals $x_3$, $y_3$ are obtained as outputs from the subtracters 48a, 48b, respectively.

The complex signals from which the low velocity signal components have been eliminated as described above are then processed by an autocorrelator 50 in order to obtain the autocorrelation of the signals $z_3$ having a delay of T.

First, the signals $z_3$ are input to delay lines 52a, 52b by which they are delayed by one period to produce signals $z_4$ as expressed by the following formulas $$z_4 = x_4 + i y_4$$

$$x_4 = -2 \sin 2\pi f_d T/2 \sin 2\pi f_d(t-T/2) \qquad (10)$$

$$y_4 = 2 \sin 2\pi f_d T/2 \cos 2\pi f_d(t-T/2) \qquad (11)$$

Then taking $z_4^* = x_4 - i y_4$, the correlation can be obtained by the following formula $$z_3 z_4^* = (x_3 + i y_3)(x_4 - i y_4) = x_3 x_4 + y_3 y_4 + i(x_4 y_3 - x_3 y_4)$$

In order to obtain this correlation, the autocorrelator 50 is provided with four multipliers 54a, 54b, 56a and 56b and with two adder-subtracters 58a, 58b.

If the output of the adder-subtracter 58a is taken as R, then from the preceding formulas (8), (9), (10) and (11), we obtain $$R = x_3 x_4 + y_3 y_4 = 4 \sin^2 2\pi f_d T/2 \cos 2\pi f_d T \qquad (12)$$

And if the output of the adder-subtracter 58b is taken as I, we obtain $$I = x_4 y_3 - x_3 y_4 = 4 \sin^2 2\pi f_d T/2 \sin 2\pi f_d T \qquad (13)$$

Then by combining the outputs from the two adder-subtracters, the following is obtained $$S = R + iI \qquad (14)$$

Next, as this output S contains the variable signal components and the noise from the apparatus, it is averaged by an averaging circuit for elimination of such extraneous components. The average is expressed by $\overline{S} = \overline{R} + i\overline{I}$, whereby the complex correlation is obtained.

In the averaging circuit, delay lines 60a, 60b produce outputs delayed by one period and these outputs are added with the inputs for the current period in the adder-subtracters 62a, 62b, whereafter the outputs obtained are fed back to the delay lines 60a, 60b and the operation is repeated. If a digital circuit is used for this addition, the average value can be obtained merely by outputting the highest order bit of the added output. However, if this operation is simply repeated, the magnitude of the output will successively increase with the increasing number of additions until at last saturation is reached. Because of this, this embodiment is provided with weighting circuits 64a, 64b for attenuating the outputs before adding them to the inputs. More specifically, by defining the amount of attenuation as $\alpha$, the signal for ten periods earlier, for example, is attenuated by a factor of $\alpha^{10}$ relative to the signal for the current period before being added to the signal for the current period. Thus the effect on the output is made small, so that an averaging effect like that of a low pass filter or a running average circuit can be obtained. Moreover, by changing the amount of weighting by the weighting circuits 64a, 64b, it is possible to adjust the degree of averaging.

Thus, as described in the foregoing, in this embodiment the correlations of the complex signals are obtained from the autocorrelator 50. These correlation outputs are input to a velocity determination circuit 66 which uses them to obtain the argument $\theta$ of the correlation outputs $\overline{S}$. More specifically, the argument $\theta$ is obtained from the formulas (12) and (13) as follows $$\theta = \tan^{-1} \frac{\overline{I}}{\overline{R}} = 2\pi \overline{f_d}\, T. \qquad (15)$$

As a result, the Doppler shift frequency $f_d$ can be very easily obtained from the argument $\theta$ as follows $$\overline{f_d} = \frac{\theta}{2\pi T}. \qquad (16)$$

In other words, since the period T at which transmission is repeated is a constant, the argument $\theta$ is proportional to the Doppler shift frequency $f_d$ or in other words is proportional to the velocity of blood flow. Moreover, as the correlations $\overline{I}$, $\overline{R}$ are taken as positive and negative, respectively, the argument $\theta$ can be measured over the range of $\pm\pi$ so that the direction of the movement can also be determined.

As in accordance with the present invention, the argument $\theta$ is obtained from $\overline{I}$ and $\overline{R}$ on the basis of formula (15), it is possible to write into a read only memory (ROM) a table of the values of the argument $\theta$ corresponding to the values assumable by $\overline{I}$ and $\overline{R}$ and to read out from the ROM the argument $\theta$ corresponding to input values of $\overline{I}$ and $\overline{R}$, thus realizing high-speed computation. This type of computation can also be applied to the various other arithmetic circuits described herein.

The Doppler signal obtained in the manner described above is converted to an analog voltage signal by a D/A converter 68 and the resulting analog signal is applied to the CRT display 30 via a switch 70 as a brightness modulation signal, whereby the velocity distribution of the movement is displayed as a picture on the CRT display 30 in either B-mode or M-mode.

In this embodiment, the CRT display 30 can selectively display either the ordinary video signal received from a video amplifier 26 or the Doppler signal, or can display both of these signals simultaneously. Thus either of the pictures can be displayed independently or they can be displayed as overlaid one on the other.

Here it should be noted that since the velocity signal is of positive or negative voltage depending on the direction of movement, it is not possible to simultaneously display velocities in both directions using ordinary brightness modulation wherein the brightness of a picture tube is varied using a voltage of only one polarity. Therefore, in this embodiment, a switch (not shown) is provided in the CRT 30 for reversing the polarity of the input signal, thus making it possible to display velocities in either direction.

Also in accordance with this invention, particularly good results can be obtained by employing a color picture tube in the CRT display 30 and displaying movements in different directions in different colors. For example, if positive velocities are displayed in red, negative velocities in blue and reflected echoes from stationary tissues in white, it becomes possible to display the tissue structure of the living organism, the direction of blood flow and the velocity of blood flow all at the same time and thus to provide high-density diagnostic information.

Although in the above-described embodiment, the low velocity signal components are removed from the complex signals by the complex delay-line canceller 44, this delay-line canceller is not absolutely necessary to this invention and may be included or excluded depending on the type of measurement to be made.

As has been described in the foregoing, in accordance with this invention, it is possible to continuously obtain the velocity distribution of movement of the moving members within the living organism, for example the velocity distribution of blood flow, along the line of passage of a sent and received ultrasonic pulse beam. As a consequence, it becomes possible to obtain highly accurate diagnostic information regarding moving members with a time delay that is only an integer multiple of the transmission pulse rate, which is to say that the distribution can substantially be displayed in real time. Moreover, clutter attributable to stationary and slow moving portions within the living organism can be suppressed through the use of delay-line canceller 44, thereby providing exceptionally high-accuracy measurement. Still further, when the beam can be held stationary, as is the case in M-mode, velocity measurement can be carried out with especially high accuracy by making the degree of averaging by the averaging circuit of the autocorrelator 50 high.

In accordance with the present invention, since wide bandwidth signals can be rapidly processed, blood flow distribution can be displayed substantially in real time in B-mode. In this case, in order to raise the response speed it is possible to make the averaging degree of the averaging circuit of the autocorrelator 50 smaller or to eliminate the averaging circuit altogether.

Again, in accordance with the present invention, since it is possible to obtain the velocity of movement of the moving menbers within the living organism using arithmetic processing employing correlation technology, the effect of random noise is minimal and it is possible to conduct measurement with a good signal-to-noise ratio.

Also the present invention makes it possible to obtain information on the velocity and velocity distribution of blood flow at the same time as obtaining the diagnostic information obtainable by a conventional ultrasonic diagnostic apparatus employing the ultrasonic echo method. The invention thus provides an ultrasonic diagnostic apparatus capable of providing large amounts of diagnostic information which is highly useful in actual practice.

What is claimed is:

1. An improved ultrasonic diagnostic apparatus including an ultrasonic probe means adapted to repeatedly transmit ultrasonic pulse beams into a living organism at a fixed pulse rate and means adapted to provide for reflected echoes to be received, amplified and displayed as the velocity of movement within the organism, the improvement comprising a complex signal converter means for converting a received high frequency signal into complex signals by mixing the received high frequency signal with a pair of complex reference signals which have frequencies that are integer multiples of the pulse rate and which are complexly related to one another, an autocorrelator means for determining the autocorrelation of said complex signal, said autocorrelator means having a time delay equal to an integer multiple of the period of the pulse rate, and a velocity determination circuit for determining the velocity utilizing said autocorrelation, whereby the velocity distribution of a moving member in the living organism is measured and displayed.

2. An ultrasonic diagnostic apparatus according to claim 1 further provided with a complex delay-line canceller means for eliminating the signal components corresponding to slow moving members of the organism from the complex signal.

* * * * *

REEXAMINATION CERTIFICATE (1578th)
United States Patent [19]
Namekawa et al.

[11] B1 4,573,477
[45] Certificate Issued  Oct. 22, 1991

[54] ULTRASONIC DIAGNOSTIC APPARATUS

[75] Inventors: Koroku Namekawa; Akira Koyano; Chihiro Kasai, all of Tokyo, Japan

[73] Assignee: Aloka Co., Ltd., Tokyo, Japan

Reexamination Request:
No. 90/002,290, Feb. 28, 1991

Reexamination Certificate for:
Patent No.: 4,573,477
Issued: Mar. 4, 1986
Appl. No.: 487,147
Filed: Apr. 21, 1983

[30] Foreign Application Priority Data

Apr. 28, 1982 [JP] Japan .................................. 57-70479

[51] Int. Cl.$^5$ .............................................. A61B 8/06
[52] U.S. Cl. ............................ 128/661.09; 73/861.25

[56] References Cited

U.S. PATENT DOCUMENTS 3,432,855  3/1969  Kalmus .
4,164,036  8/1979  Wax .
4,398,540  8/1983  Takemura et al. .

FOREIGN PATENT DOCUMENTS 0014793   9/1980   European Pat. Off. .
0073418   3/1983   European Pat. Off. .
49-107772 10/1974  Japan .
51-126171  1/1976  Japan .
51-136443 11/1976  Japan .
53-46188   4/1978  Japan .
55-54942   4/1980  Japan .
55-82066   6/1980  Japan .
56-34329   4/1981  Japan .
57-11644   1/1982  Japan .

OTHER PUBLICATIONS

Gerzberg, L., et al. (1980), "Power-Spectrum Centroid Detection for Doppler Systems Applications"; Ultrasonic Imaging 2, pp. 232-261.

Novick, L. R., et al. (1975), "Spectral Mean and Variance Estimation Via Pulse Pair Processing"; 16th Radar Meteorology Conference, Apr. 22-24, 1975, Session 1, pp. 1-5.

*Primary Examiner*—Ruth S. Smith

[57] ABSTRACT

An ultrasonic diagnostic apparatus for accurately displaying the velocity distribution of moving members within a living organism. The apparatus constitutes an improvement on the ultrasonic diagnostic apparatus of the type wherein an ultrasonic pulse beam is repeatedly transmitted into the living organism at a fixed pulse rate and the reflected echoes are picked up, amplified and displayed, wherein the improvement comprises a complex signal converter for converting a received high frequency signal into complex signals by mixing the received high frequency signal with a pair of complex reference signals which have frequencies that are integer multiples of the pulse rate and which are complexly related to one another, an autocorrelator for determining the autocorrelation of the complex signals, the autocorrelator having a delay time equal to an integer multiple of the pulse period, and a velocity determination circuit for determining the velocity through said autocorrelation. The apparatus is capable of measuring the velocity distribution of moving members within the organism and of rapidly displaying the measured results in real time.

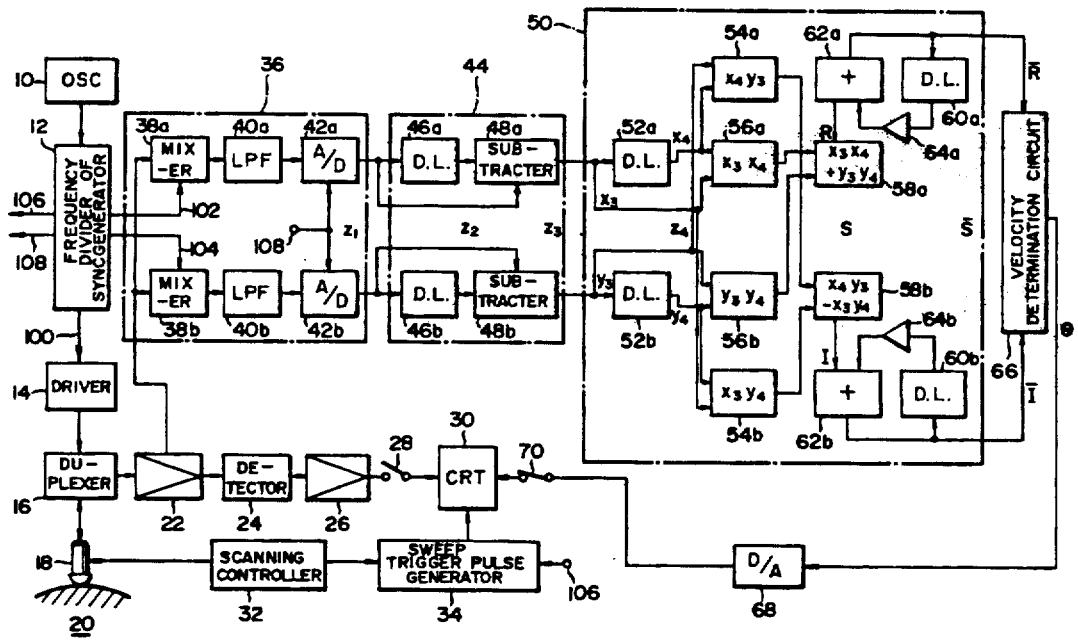

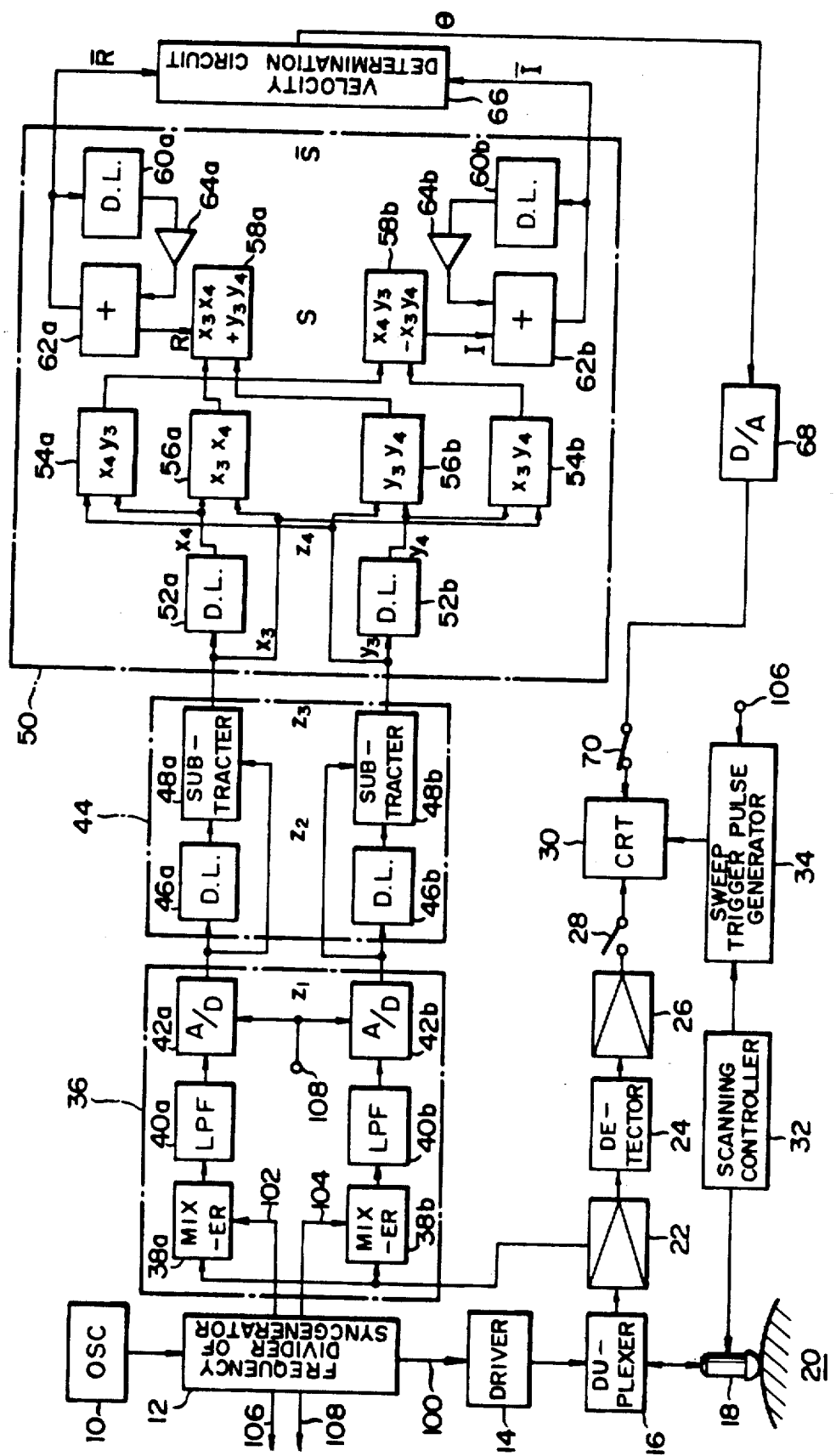

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 2 is confirmed.

* * * * *